United States Patent [19]

Armstrong

[11] 4,303,643

[45] Dec. 1, 1981

[54] SULFONAMIDE COMPOSITIONS

[75] Inventor: William W. Armstrong, Mill Neck, N.Y.

[73] Assignee: Pfizer Inc., New York, N.Y.

[21] Appl. No.: 170,490

[22] Filed: Jul. 21, 1980

Related U.S. Application Data

[63] Continuation of Ser. No. 54,546, Jul. 5, 1979, abandoned.

[51] Int. Cl.³ .................. A61K 31/79; A61K 31/625; A61K 31/505
[52] U.S. Cl. ..................................... 424/80; 424/229; 424/251
[58] Field of Search ........................ 424/229, 80, 251

[56] References Cited

U.S. PATENT DOCUMENTS

| | | | |
|---|---|---|---|
| 3,551,564 | 12/1970 | Klaui et al. | 424/229 |
| 3,985,876 | 10/1976 | Hazlett et al. | 424/229 |
| 4,018,889 | 4/1977 | Armstrong | 424/80 |

*Primary Examiner*—Jerome D. Goldberg
*Attorney, Agent, or Firm*—Charles J. Knuth; Allen J. Spiegel

[57] ABSTRACT

Aqueous parenteral solutions of from about 10 to 20% w/v of sulfamethoxazole or sulfadoxine and about 3 to 5% w/v of trimethoprim in from 60 to 80% w/v of 2-pyrrolidone are disclosed.

3 Claims, No Drawings

SULFONAMIDE COMPOSITIONS

CROSS-REFERENCE TO RELATED APPLICATION

This application is a continuation of copending application Ser. No. 54,546, filed July 5, 1979, now abandoned.

BACKGROUND OF THE INVENTION

This invention relates to sulfonamide solutions suitable for pharmaceutical use. More particularly, it relates to aqueous parenteral solutions of sulfamethoxazole or sulfadoxine with trimethoprim in 2-pyrrolidone.

Antibacterial compositions containing sulfamethoxazole and trimethoprim are disclosed in U.S. Pat. No. 3,515,783.

Parenteral solutions of sulfamethoxazole and trimethoprim containing the following water-miscible solvents are disclosed in U.S. Pat. No. 3,551,564: polyethyleneglycol ethers of tetrahydrofurfuryl alcohol, dimethylformamide, dimethylsulfoxide, dimethylacetamide, diethylacetamide, 1,2-propyleneglycol, di-(1,2-propyleneglycol), 1,3-butylene glycol, glycerol formal, diethylene glycol and polyethylene glycol containing 2-15 ethylene oxide groups.

U.S. Pat. No. 3,985,876 discloses solutions of trimethoprim with various sulfonamides, including sulfamethoxazole and sulfadoxine in a mixture of 10-60% water and 30-90% organic solvents such as dimethyl and diethylacetamide, dimethyl formamide, dimethylsulfoxide, glycerol formal and various glycols.

U.S. Pat. No. 4,018,889 discloses oxytetracycline solutions containing from about 1 to 40% oxytetracycline in an aqueous vehicle containing from about 10 to 50% by weight of 2-pyrrolidone, about 0.8 to 1.3 molar proportions of a pharmaceutically acceptable magnesium compound soluble in the said solution, said solution having a pH value in the range of from about 7.5 to 9.5.

SUMMARY OF THE INVENTION

In accordance with this invention there is disclosed an aqueous parenteral solution of sulfamethoxazole or sulfadoxine and trimethoprim in 2-pyrrolidone.

This invention further discloses a liquid sulfonamide composition comprising an aqueous solution of from about 10 to 20% w/v of sulfamethoxazole or sulfadoxine, about 3 to 5% w/v of trimethoprim in from about 60 to 80% w/v of 2-pyrrolidone, said composition having a pH of from about 5 to 9.5.

DETAILED DESCRIPTION OF THE INVENTION

The sulfonamides utilized in the compositions of this invention are sulfamethoxazole and sulfadoxine. They are present in concentrations of from about 10 to 20% w/v. The preferred concentration is about 20% w/v.

Sulfamethoxazole [$N^1$-(5-methyl-3-isoxazolyl)sulfonilamide] is particularly described in U.S. Pat. No. 2,888,455.

Sulfadoxine [$N'$-(5,6-dimethoxy-4-pyrimidyl)sulfonilamide] is described in U.S. Pat. No. 3,132,139.

Trimethoprim is also utilized in the compositions of this invention as a potentiator in concentrations of from about 3 to 5% w/v. The preferred concentration is about 4% w/v.

Trimethoprim [2,4-diamino-5-(3,4,5-trimethoxybenzyl)pyrimidine] is described in U.S. Pat. No. 2,909,522.

2-Pyrrolidone is present as a co-solvent for the sulfonamide and trimethoprim in a concentration of from about 60 to 80% w/v.

2-Pyrrolidone is also known as 2-pyrrolidinone, 2-oxopyrrolidine, alpha-pyrrolidone and 2-ketopyrrolidine. It has an oral $LD_{50}$ of 8 gm/kg in rats and 3.8 gm/kg by intraperitoneal injection in mice.

The pH value of these compositions is adjusted if necessary to pH 5 to 9.5. The pH can be adjusted by means of a base that is pharmaceutically acceptable, such as monoethanolamine.

As an optional ingredient polyvinylpyrrolidone having a molecular weight of between about 5,000 and 100,000 (K-12 to 30) may also be present in these compositions in a concentration of from about 1 to 5% w/v. The polyvinylpyrrolidone preferred for this invention is one having an average molecular weight of about 10,000-17,000 (where K-value=17). It is present in part as a cosolubilizer and may improve tissue toleration.

As optional consolvents ingredients such as propylene glycol, polyethylene glycols, benzyl alcohol, dimethylacetamide, ethyl lactate and glycerol formal may be present at concentrations of from about 0.5 to 30% w/v.

The stability of these solutions for therapeutic administration is still further enhanced by use of an antioxidant such as monothioglycerol at levels of from about 0.1 to 1% w/v.

The primary application of these sulfonamide compositions is as a parenteral composition but the new compositions can also be used for topical application.

These solutions produce efficacious blood levels and are well tolerated in contrast to the short term blood levels and tissue damage routinely experienced with presently available highly alkaline aqueous sulfonamide solutions.

The sulfonamide antibiotic compositions of this invention are also easy to syringe over a wide temperature range and are satisfactory from a physical and chemical stability standpoint. The compositions of this invention are preferably prepared by mixing the 2-pyrrolidone with water and other cosolvents, if present. The sulfonamide and trimethoprim are then added and stirred until a clear solution results. The pH is then adjusted to the desired range. If polyvinylpyrrolidone is to be included, it is added to the water at the time of mixing the 2-pyrrolidone.

The present invention is illustrated by the following examples. However, it should be understood that the invention is not limited to the specific details of the examples.

EXAMPLES 1-3

|  | gm/100 ml | | |
|---|---|---|---|
|  | Example 1 | Example 2 | Example 3 |
| Sulfamethoxazole | 20.00 | 20.00 | 20.00 |
| Timethoprim | 4.00 | 4.00 | 4.00 |
| 2-Pyrrolidone | 60.00 | 60.00 | 70.00 |
| Dimethylacetamide | — | — | 10.00 |
| Polyvinylpyrrolidone (K = 17) | 5.00 | 5.00 | — |
| Glycerol formal | — | 20.00 | — |
| Benzyl alcohol | 0.90 | 0.90 | 0.90 |
| Monothioglycerol | 0.20 | 0.20 | 0.20 |
| Monoethanolamine | 4.50 | 4.50 |  |

-continued

|  | gm/100 ml | | |
|---|---|---|---|
|  | Example 1 | Example 2 | Example 3 |
| Water q.s. to | 100.00 | 100.00 | 100.00 |
| pH | 8.8 | 8.8 | 7.0 |
| Viscosity cts at 25° C. | 35 | 31 | 28 |

The above solutions were prepared by dissolving all the ingredients in water, with the sulfamethoxazole and trimethoprim being added last.

Raising the pH of Examples 1 and 2 with monoethanolamine to pH 9.5 and 8.8 respectively produced similar solutions with no significant viscosity changes.

EXAMPLES 4-5

|  | gm/100 ml | |
|---|---|---|
|  | Example 4 | Example 5 |
| Sulfadoxine | 20.00 | 20.00 |
| Trimethoprim | 4.00 | 4.00 |
| 2-Prrolidone | 60.00 | 70.00 |
| Polyvinylpyrrolidone (K = 17) | 5.00 | 5.00 |
| Dimethylacetamide | 10.00 | 10.00 |
| Glycerol formal | 7.50 | 7.50 |
| Benzyl alcohol | 0.90 | 0.90 |
| Monothioglycerol | 0.20 | 0.20 |
| Monoethanolamine | 2.00 | — |
| Water q.s. to | 100.00 | 100.00 |
| pH | 8.7 | 7.7 |
| Viscosity cts at 25° C. | 49 | 53 |

The above solutions were prepared by dissolving all the ingredients in water, with the sulfadoxine and trimethoprim being added last.

EXAMPLES 6-8

|  | gm/100 ml | | |
|---|---|---|---|
|  | Example 6 | Example 7 | Example 8 |
| Sulfadoxine | 20.00 | 20.00 | 20.00 |
| Trimethoprim | 4.00 | 4.00 | 4.00 |
| 2-Pyrrolidone | 80.00 | 80.00 | 70.00 |
| Polyvinylpyrrolidone (K = 17) | 5.00 | — | — |
| Dimethylacetamide | 10.00 | 10.00 | 10.00 |
| Benzyl alcohol | 0.90 | 0.90 | 0.90 |
| Monothioglycerol | 0.20 | 0.20 | 0.20 |
| Monoethanolamine | — | — | 2.00 |
| Water q.s. to | 100.00 | 100.00 | 100.00 |
| pH | 7.9 | 8.0 | 8.4 |
| Viscosity cts at 25° C. | 63 | 28 | 26 |

The above solutions were prepared by dissolving all the ingredients in water, with the sulfadoxine and trimethoprim being added last.

I claim:

1. A liquid sulfonamide composition comprising an aqueous solution of from about 10 to 20% w/v of sulfamethoxazole and about 3 to 5% w/v of trimethoprim in from about 60 to 80% w/v of 2-pyrrolidone, said composition having a pH of from about 5 to 9.5.

2. A composition as claimed in claim 1 wherein polyvinylpyrrolidone is also present in a concentration of from about 1 to 5% w/v.

3. A sulfonamide composition comprising an aqueous solution of about 20% w/v sulfamethoxazole, about 4% w/v trimethoprim, from about 60 to 80% w/v 2-pyrrolidone and from about 1 to 5% w/v of polyvinylpyrrolidone, said composition having a pH value in the range of from about 7 to 9.5.

* * * * *